(12) United States Patent
Fallone et al.

(10) Patent No.: US 9,468,777 B2
(45) Date of Patent: Oct. 18, 2016

(54) INTEGRATED EXTERNAL BEAM RADIOTHERAPY AND MRI SYSTEM

(75) Inventors: B. Gino Fallone, Alberta (CA); Marco Carlone, Alberta (CA); Brad Murray, Alberta (CA)

(73) Assignee: Alberta Health Services, Edmonton, Alberta (CA)

( * ) Notice: Subject to any disclaimer, the term of this patent is extended or adjusted under 35 U.S.C. 154(b) by 753 days.

(21) Appl. No.: 12/090,586

(22) PCT Filed: Oct. 10, 2006

(86) PCT No.: PCT/CA2006/001656
§ 371 (c)(1),
(2), (4) Date: Oct. 23, 2008

(87) PCT Pub. No.: WO2007/045076
PCT Pub. Date: Apr. 26, 2007

(65) Prior Publication Data
US 2009/0149735 A1    Jun. 11, 2009

Related U.S. Application Data

(60) Provisional application No. 60/726,613, filed on Oct. 17, 2005, provisional application No. 60/779,971, filed on Mar. 8, 2006.

(51) Int. Cl.
*A61B 5/05* (2006.01)
*A61N 5/10* (2006.01)
*A61B 5/055* (2006.01)

(52) U.S. Cl.
CPC ............ *A61N 5/1049* (2013.01); *A61B 5/055* (2013.01); *A61N 5/1081* (2013.01); *A61N 2005/1055* (2013.01)

(58) Field of Classification Search
CPC ................ A61B 6/405; A61B 6/4064; A61N 2005/1055
USPC ........ 600/407, 410, 411, 415, 425, 427, 436
See application file for complete search history.

(56) References Cited

U.S. PATENT DOCUMENTS 5,422,926 A * 6/1995 Smith et al. .................. 378/121
5,434,420 A * 7/1995 McKeown et al. ....... 250/396 R
(Continued)

FOREIGN PATENT DOCUMENTS

| JP | 2001-517132 A | 10/2001 |
|----|---------------|---------|
| JP | 2003-225315 A | 8/2003  |

(Continued)

OTHER PUBLICATIONS

Raaymakers, B., Integrating a MRI scanner with a 6 MV radiotherapy accelerator: dose deposition in a transverse magnetic field, Phys. Med. Biol. 49 (2004) 4109-4118.*

(Continued)

*Primary Examiner* — Rajeev Siripurapu
(74) *Attorney, Agent, or Firm* — Alston & Bird LLP

(57) ABSTRACT

A radiation therapy system comprises a radiation source generating a beam of radiation and a magnetic resonance imaging apparatus. An interface acts between the radiation source and the MRI apparatus that permits irradiation to be performed simultaneously with imaging. The MRI apparatus and radiation source are coupled such that the system can be used in a rotation mode whereby the radiation source can irradiate a subject from basically any angle without reducing MRI image quality.

16 Claims, 5 Drawing Sheets

(56) References Cited

U.S. PATENT DOCUMENTS

| | | | |
|---|---|---|---|
| 5,538,494 A | 7/1996 | Matsuda | |
| 5,651,043 A | 7/1997 | Tsuyuki et al. | |
| 5,851,182 A * | 12/1998 | Sahadevan | 600/407 |
| 5,977,530 A * | 11/1999 | Bessho et al. | 219/715 |
| 6,175,761 B1 | 1/2001 | Frandsen et al. | |
| 6,198,957 B1 | 3/2001 | Green | |
| 6,366,641 B1 * | 4/2002 | Whitham | 378/65 |
| 6,366,798 B2 | 4/2002 | Green | |
| 6,708,054 B2 | 3/2004 | Shukla et al. | |
| 6,862,469 B2 | 3/2005 | Bucholz et al. | |
| 6,993,112 B2 | 1/2006 | Hesse | |
| 7,221,733 B1 | 5/2007 | Takai et al. | |
| 7,227,925 B1 | 6/2007 | Mansfield et al. | |
| 7,245,698 B2 | 7/2007 | Pang et al. | |
| 7,289,599 B2 | 10/2007 | Seppi et al. | |
| 7,349,522 B2 | 3/2008 | Yan et al. | |
| 7,352,370 B2 | 4/2008 | Wang et al. | |
| 7,375,357 B2 | 5/2008 | Kaufman | |
| 7,415,095 B2 | 8/2008 | Wofford et al. | |
| 7,443,946 B2 | 10/2008 | Deller et al. | |
| 7,450,687 B2 | 11/2008 | Yeo et al. | |
| 7,453,976 B1 | 11/2008 | Yin | |
| 7,551,717 B2 | 6/2009 | Tome et al. | |
| 7,567,694 B2 | 7/2009 | Lu et al. | |
| 7,574,251 B2 | 8/2009 | Lu et al. | |
| 7,596,207 B2 | 9/2009 | Kaus et al. | |
| 7,609,810 B2 | 10/2009 | Yi et al. | |
| 7,639,854 B2 | 12/2009 | Schnarr et al. | |
| 7,643,661 B2 | 1/2010 | Ruchala et al. | |
| 7,853,308 B2 | 12/2010 | Sauer et al. | |
| 7,989,987 B2 * | 8/2011 | McDonald | 307/108 |
| 8,042,209 B2 | 10/2011 | D'Souza et al. | |
| 8,073,102 B2 | 12/2011 | Fallone et al. | |
| 8,229,068 B2 | 7/2012 | Lu et al. | |
| 2001/0001807 A1 | 5/2001 | Green | |
| 2001/0041835 A1 * | 11/2001 | Front et al. | 600/429 |
| 2001/0049474 A1 * | 12/2001 | Wagshul | 600/411 |
| 2002/0123682 A1 * | 9/2002 | Allred et al. | 600/411 |
| 2003/0004405 A1 * | 1/2003 | Townsend et al. | 600/407 |
| 2003/0174808 A1 * | 9/2003 | Hughes et al. | 378/65 |
| 2005/0197564 A1 | 9/2005 | Dempsey | |
| 2005/0201516 A1 | 9/2005 | Ruchala et al. | |
| 2005/0267350 A1 * | 12/2005 | McKinnon | 600/407 |

FOREIGN PATENT DOCUMENTS

| | | |
|---|---|---|
| JP | 2004-166975 A | 6/2004 |
| WO | WO 99/32189 A1 | 7/1999 |
| WO | WO 01/74440 | 10/2001 |
| WO | WO 03/076016 A1 | 9/2003 |
| WO | WO 2004/024235 | 3/2004 |
| WO | WO 2005/031629 | 4/2005 |
| WO | WO 2007/014026 A2 | 2/2007 |
| WO | WO 2007/014105 A2 | 2/2007 |

OTHER PUBLICATIONS

Marbach, J.R., Management of Radiation Oncology Patients with Implanted Cardiac Pacemakers, AAPM Report No. 45 (1994); Medical Physics vol. 21, Issue 1 (1994).*

Kirkby, C. et al., *Patent Dosimetry for Mybrid MR1-Radiotherapy Systems*, Med. Phys. vol. 35, No. 3, Mar. 2008, pp. 1019-1027.

Bielajew, A. F., *The Effect of Strong Longitudinal Magnetic Fields on Dose Deposition From Electron and Photon Beams*, Med. Phys. vol. 20, No. 4, Jul./Aug. 1993, pp. 1171-1179.

International Search Report and Written Opinion of the International Searching Authority for International Application No. PCT/CA2006/001656.

Supplementary European Search Report for EP 06 79 0814 completed Aug. 27, 2009.

Office Action for European Application No. 06 790 814.5 dated Nov. 13, 2009.

Office Action for Chinese Application No. 200680046233.9 dated Mar. 10, 2010.

Office Action for U.S. Appl. No. 12/090,591 dated May 11, 2010.

Final Office Action for U.S. Appl. No. 12/090,591 dated Jan. 21, 2011.

Notice of Allowance for U.S. Appl. No. 12/090,591 dated May 25, 2011.

Office Action for U.S. Appl. No. 13/305,123 dated Nov. 1, 2013.

Office Action for Canadian Application No. 2,626,538 dated May 30, 2014.

Office Action for Japanese Application No. 2013-097688 received Apr. 16, 2014.

Office Action for U.S. Appl. No. 13/305,123 dated May 29, 2014.

Decision of Rejection from Japanese Patent Application No. 2013-097688, dated Oct. 7, 2014.

Office Action from U.S. Appl. No. 13/305,123 dated Dec. 16, 2014.

Notice of Allowance for U.S. Appl. No. 13/305,123 dated Sep. 25, 2014.

* cited by examiner

INTEGRATED EXTERNAL BEAM RADIOTHERAPY AND MRI SYSTEM

FIELD OF THE INVENTION

The present invention relates generally to radiation therapy and in particular to an integrated external beam radiotherapy and magnetic resonance imaging (MRI) system.

BACKGROUND OF THE INVENTION

Radiation therapy can be given to treat proliferative tissue disorders including but not limited to cancer, arteriovenous malformations, dermatological lesions etc. During radiation therapy, the tissue of the patient known to or suspected to contain the disease is exposed to radiation. Linear accelerators are commonly used to irradiate a target volume encompassing the tissue to be treated during radiation therapy. As is known, linear accelerators use microwave technology to accelerate electrons in a waveguide and then allow the electrons to collide with a heavy metal target. As a result of the collisions, high-energy x-rays are scattered from the target. A portion of the scattered x-rays is collected and shaped by a beam collimating device to form an output beam of radiation conforming to the shape of the target volume. The linear accelerator also includes a gantry that rotates around the patient allowing the output beam of radiation to be delivered to the desired target volume from any angle by rotating the gantry.

Prior to exposing a patient to radiation, a treatment plan is typically developed in order to determine accurately the location of the tissue to be treated and how best to treat the tissue with radiation. Many imaging techniques have been used in treatment planning such as for example, computed tomography (CT), magnetic resonance imaging (MRI), and nuclear scintigraphy including single photon emission tomography (SPECT) and positron emission tomography (PET). Acquired images of the tissue are used to define the target volume so that the actual tissue irradiated by the output beam of radiation conforms as much as possible to the target volume. In many instances, the images of the tissue used to define the target volume are acquired in a single simulation.

For dose delivery, techniques such as tumour immobilisation with IMRT and image guidance have commonly been utilized. The purpose of image guidance is to ensure that the target tissue is placed at the isocenter of the linear accelerator at the beginning of radiation treatment. In tissue sites where a large amount of tissue motion is expected (for instance lung cancer radiotherapy), image guided therapy also constitutes control of the output beam of radiation to ensure that the irradiation time is restricted to the moment when the tissue is localized at the linear accelerator isocenter.

Unfortunately, this method has a fundamental difficulty if the image used to define the target volume is acquired in a single simulation since it is not known if image guided reproduction of the target location in subsequent treatment fractions results in the planned dosimetry being accurately delivered to the target and non-target tissues. This is because it is not known, a priori, if the single simulation image is representative of the patient positioning and target volume configuration in subsequent radiotherapy treatment fractions.

To provide more accurate position information concerning the target tissue and ensure the beam of radiation is properly directed in subsequent radiotherapy treatment fractions, it has been considered to integrate a linear accelerator with a magnetic resonance imaging apparatus.

MRI is a well-known imaging technique. During MRI, a target, typically a human patient, is placed into an MRI machine and subjected to a uniform magnetic field produced by a polarizing magnet housed within the MRI machine. Radio frequency (RF) pulses, generated by an RF coil housed within the MRI machine in accordance with a particular localization method, are used to scan target tissue of the patient. MRI signals are radiated by excited nuclei in the target tissue in the intervals between consecutive RF pulses and are sensed by the RF coil. During MRI signal sensing, gradient magnetic fields are switched rapidly to alter the uniform magnetic field at localized areas thereby allowing spatial localization of MRI signals radiated by selected slices of the target tissue. The sensed MRI signals are in turn digitized and processed to reconstruct images of the target tissue slices using one of many known techniques.

Integrating a linear accelerator with an MRI apparatus poses several technical problems. For example, the magnetic field generated by the MRI apparatus interferes with the operation of the linear accelerator. In particular, the magnetic field generated within the MRI apparatus interferes with the trajectory of the electron beam in the linear accelerator through the magnetic force $F=qvB$ and can cause the electron beam to deflect. For a strong magnetic field, the deflection can be great enough to force the accelerated electron beam into the accelerating waveguide and prevent it from reaching the heavy metal target at the output of the accelerating waveguide. Even for a partially deflected electron beam, the altered angle of incidence on the heavy metal target may cause sufficient perturbation to the bremstrahlung x-ray beam to cause it to be unacceptable clinically.

In addition, the presence of the linear accelerator perturbs the magnetic field generated by the MRI apparatus. For modern radiotherapy, it is required to move the beam of radiation relative to the patient, in order to conform the radiotherapy to the shape of the target volume. A large amount of material that is placed in the fringe magnetic field of the MRI magnet will cause alteration of the magnetic field lines, which could extend to the homogeneous region of the magnet. This in itself is not a problem since this can be compensated for; however, if this material is moved (for instance if this material were a linear accelerator, or the shielding surrounding a cobalt source), the dynamic perturbation of the magnetic field in the homogeneous region could cause unacceptable image distortions. This problem would exist for both linear accelerator and cobalt based radiotherapy.

Still further problems exist in that the RF fields generated by the linear accelerator interfere with the receiver coils of the MRI apparatus. The linear accelerator works in a pulsed power mode, where microwave frequency RF is generated by pulsing a high voltage current to a microwave generator (a klystron or magnetron), which creates suitable RF power that is transported through a transmission waveguide to the accelerating waveguide. The accelerating waveguide is a periodic structure that generates electric fields that are suitable to accelerate electrons to a Megavoltage energy. The RF fields generated by the linear accelerator are contained in these resonant, transmission and accelerating structures such that no appreciable power will leak out and interfere with the MRI apparatus operation. However, the pulsed power modulator generates high voltage (typically 50 to 100 kV at large currents 70 to 110 A) pulses of typically 4 microsecond duration. The rise and fall times are typically less than 1 microsecond. The frequency spectrum of the pulse contains a component in the MHz range that generates a noise signal of sufficient power that will significantly interfere with the RF receiver coils of the MRI apparatus. The exact frequency and power level of the modulator noise depends on the shape of the modulator high voltage pulse, and the mechanical characteristics of the high voltage circuitry and structure housing the high voltage circuit.

U.S. Pat. No. 6,366,798 to Green discloses a radiotherapy machine including a magnetic resonance imaging system. The radiotherapy machine treats a region of a subject while the region and volumes abutting the region are imaged by the magnetic resonance imaging system. The beam and an excitation coil assembly of the imaging system are arranged so that the beam is not incident on the coil assembly. The excitation coil assembly includes two spaced winding segments for producing a main DC magnetic field. The segments are located on opposite sides of the region. A treatment couch for the subject fits within aligned central openings of the winding segments. The coil assembly produces main magnetic field lines that extend generally in the same direction as the axis about which the beam turns. Mutual interference issues, which arise from placing a rotating beam generator in a stationary magnetic resonance imaging system, are not discussed.

U.K. Patent Document No. 2 393 373 to Lagendijk discloses a linear accelerator integrated with an MRI apparatus. Components and systems are provided that prevent, among other difficulties, the magnetic field of the MRI apparatus to interfere with the operation of the linear accelerator.

U.S. Patent Application Publication No. 2005/0197564 to Dempsey discloses a device and process for performing MR imaging during radiation therapy by using a Helmholtz-pair coil MRI system in conjunction with a cobalt source of radiation. The significant shielding required for the cobalt source may corrupt MR image quality during rotation.

As will be appreciated, there exists a need for an improved integrated linear accelerator and MRI apparatus that obviates or mitigates at least one of the above-identified disadvantages. It is therefore an object of the present invention to provide a novel integrated external beam radiotherapy and magnetic resonance imaging (MRI) apparatus.

SUMMARY OF THE INVENTION

Accordingly, in one aspect there is provided a radiation therapy system comprising:
a radiation source capable of generating a beam of radiation;
a magnetic resonance imaging (MRI) apparatus; and
an interface between the radiation source and the MRI apparatus that permits irradiation to be performed simultaneously with imaging, wherein the MRI apparatus and radiation source are coupled such that the system can be used in a rotation mode whereby the radiation source can irradiate a subject from basically any angle without reducing MRI image quality.

The radiation source may be a linac, other particle accelerator including those that use laser-induced plasmas, that generate electromagnetic radiation (such as photons, x-rays, coherent radiations), electrons, protons, carbon ions, other heavy ions, neutrons or sub-atomic particles such as pi-mesons, a radioisotope source, a radiation generating device that radiates electromagnetic, sound, heat, UV etc or a source of coherent radiation such as for example a synchrotron.

In one embodiment, the radiation source can be rotated without affecting the homogeneity of the MRI magnetic field. Alternatively, in another embodiment, the radiation source and MRI apparatus are held stationary with rotation therapy being achieved through rotation of the subject.

In one embodiment, pulsing of the radiation source does not occur at the same time as RF signal read-back of the MRI apparatus. Also, RF noise that can interfere with the RF signal read-back of the MRI apparatus is reduced.

According to another aspect there is provided an integrated radiation source and magnetic resonance imaging (MRI) system comprising:
a radiation source;
an MRI apparatus;
a coupling to couple the radiation source and the MRI apparatus; and
interference reducing structure to inhibit the radiation source and MRI apparatus from interfering with one another during operation.

In one embodiment, the coupling couples the radiation source and the MRI apparatus so that the radiation source does not effect the magnetic field generated by the MRI apparatus during movement of the radiation source and/or MRI apparatus. In one embodiment, this is achieved by moving the radiation source and MRI apparatus in unison. The coupling may couple a gantry of the radiation source and a gantry of the MRI apparatus or may couple the radiation source and MRI apparatus to a common gantry.

The interference reducing structure may include a beam steering apparatus to maintain the position of the electron beam generated by the radiation source. In this case, the beam steering apparatus includes beam position sensor and steering coil arrangements disposed along an accelerating waveguide of the radiation source.

In another embodiment, the system further comprises a two-dimensional imaging device. The imaging device captures one of megavoltage axial and computed tomography images simultaneously with MR images for beam verification, registration and generation of attenuation data used in treatment planning calculations. Alternatively or in conjunction with, the imaging device captures SPECT images simultaneously with MR images for improved diagnostic information and treatment planning.

According to yet another aspect there is provided an integrated radiation source and magnetic resonance imaging (MRI) system comprising:
a radiation source;
an MRI apparatus;
a coupling to couple the radiation source and the MRI apparatus, wherein operation of said radiation source and MRI apparatus are timed to inhibit the radiation source and MRI apparatus from interfering with one another during operation.

In one embodiment, radiation source driving pulses are interrupted during MRI apparatus RF signal reading. Also, RF noise generated by the radiation source that can interfere with MRI apparatus RF signal reading is reduced by shaping the radiation source driving pulses.

The integrated radiation source and MRI system allows the radiation source and MRI apparatus to operate effectively without the radiation source and MRI apparatus interfering with one another during operation. This allows images of the subject to be captured and used to ensure that the beam of radiation generated by the radiation source is directed properly to the target tissue during radiotherapy treatment fractions.

BRIEF DESCRIPTION OF THE DRAWINGS

Embodiments will now be described more fully with reference to the accompanying drawings in which.

DETAILED DESCRIPTION OF THE EMBODIMENTS

Figure 1:
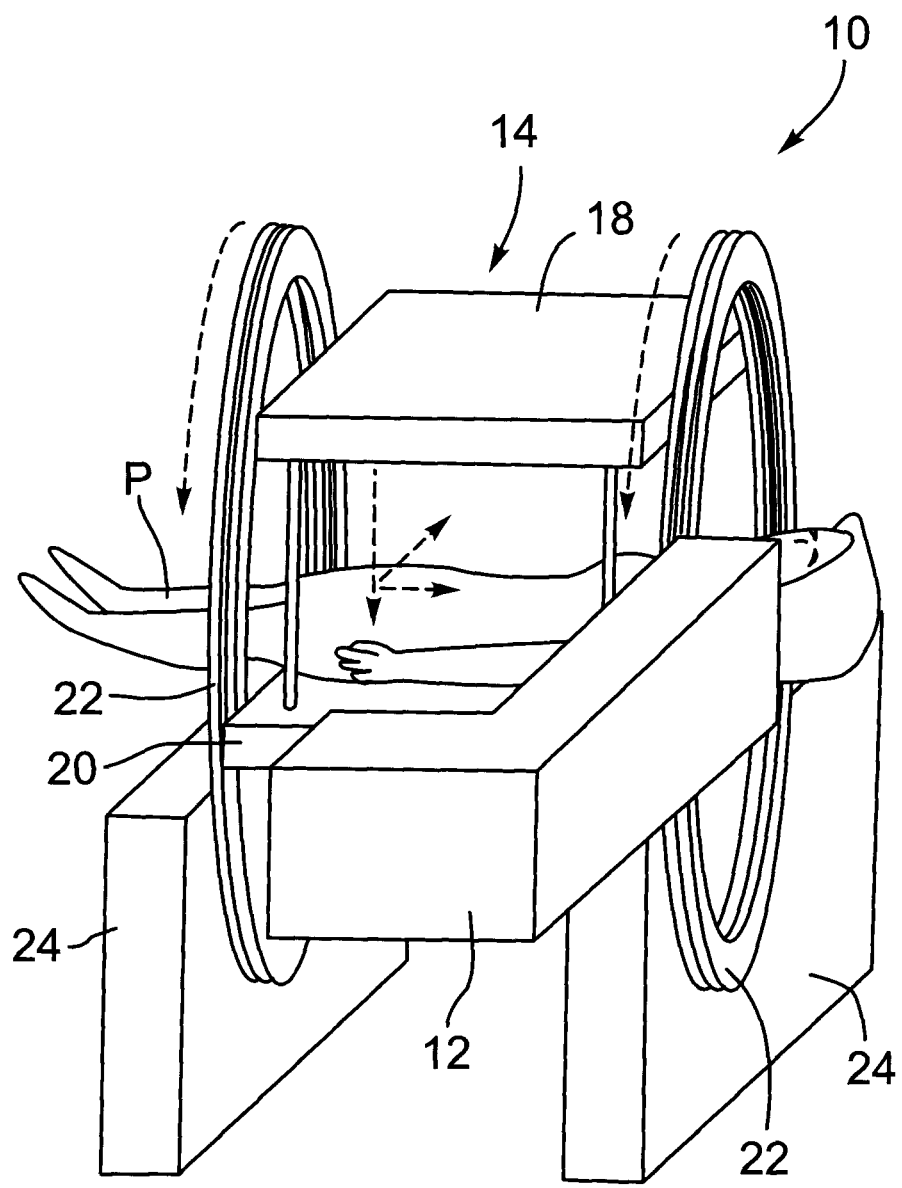
FIG. 1 is a partial schematic, perspective view of an integrated linear accelerator and MRI system in one orientation.
Figure 2:
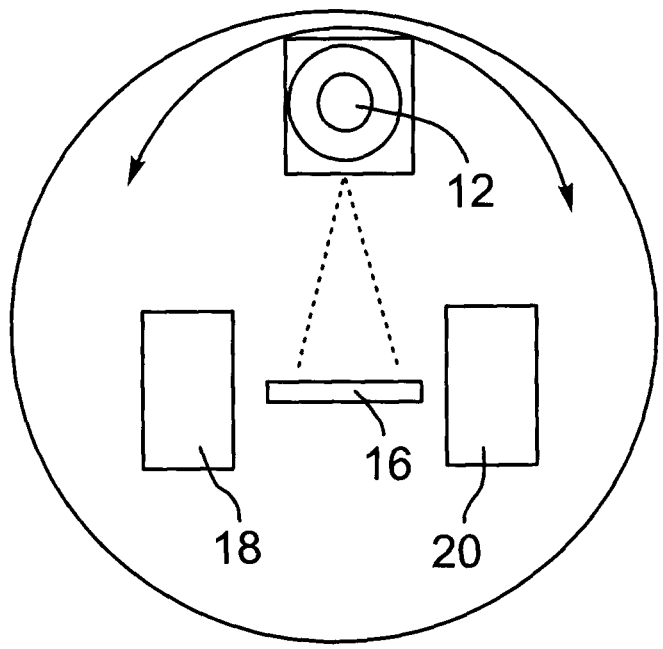
FIG. 2 is a view in a transverse plane of the integrated linear accelerator and MRI system of FIG. 1 in another orientation.
Figure 3:
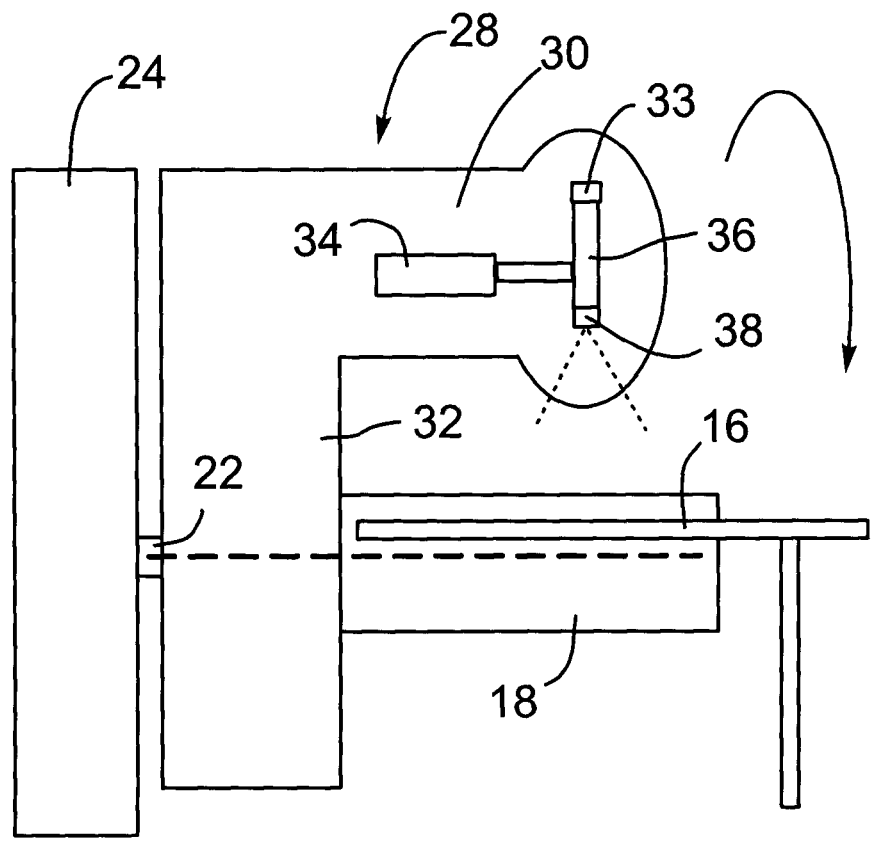
FIG. 3 is a view in a saggital plane of the integrated linear accelerator and MRI system of FIG. 1.

Turning now to FIGS. 1 to 3, an integrated linear accelerator and MRI system is shown and is generally identified by reference numeral 10. As can be seen, the integrated linear accelerator and MRI system 10 includes a linear accelerator ("linac") 12 and an MRI apparatus 14. Linac within the context of the present application refers to virtually any radiation source, such as for example a particle accelerator or radioisotope source, capable of generating a beam of radiation including for example x-rays, gamma rays, electrons, protons, helium ions, carbon ions, other heavy ions or neutrons.

In this particular example, the MRI apparatus 14 has a 0.2 T magnetic field strength and is of the open bore type including a table 16 on which a patient P can lay and be moved into and out of the opening for the magnet/linac. The poles 18 and 20 of a polarizing magnet are disposed above and below the table 16. The magnet poles 18 and 20 are mounted on a rotating gantry 22 that is supported by a frame 24.

The linac 12 includes a head 28 housing an electron beam generator 30 mounted on an arm 32 that is affixed to the gantry 22. In this manner, the linac 12 rotates in unison with the gantry 22 and thus, maintains its position relative to the magnet poles 18 and 20. Of course if desired, the linac 12 may have its own gantry. In this case, the gantry of the linac 12 and the gantry 22 are mechanically coupled so that the linac 12 rotates in unison with the magnet poles 18 and 20.

Figure 4:
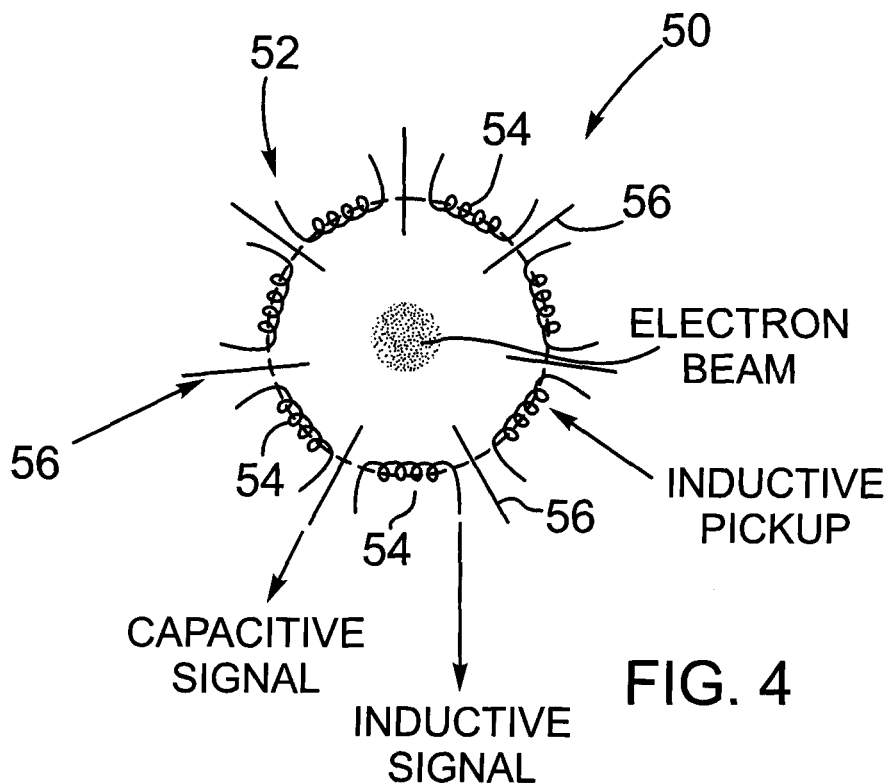
FIG. 4 is an end view of an accelerating waveguide and beam steering apparatus forming part of the linear accelerator.

The electron beam generator 30 includes an electron gun 33, an RF generator 34, an accelerating waveguide 36, a heavy metal target 38 at one end of the accelerating waveguide 36 and a beam collimating device (not shown). A beam steering apparatus 50 is also provided as shown in FIG. 4 to inhibit magnetic fields generated by the MRI apparatus 14 from interfering with linac operation. As will be appreciated, a magnetic field of 5 Gauss has the potential to disrupt operation of the linac since magnetic fields of as low as 1-2 Gauss may steer an electron beam in clinical linacs.

The beam steering apparatus 50 includes electron beam position sensor and steering coil arrangements 52 disposed along the accelerating waveguide 36. Each position sensor and steering coil arrangement includes inductive pickup coils 54 arranged in a ring around the accelerating waveguide 36 with capacitive sensors 56 interposed between each inductive pickup coil. The pick-up coils 54 and sensors 56 sense when the electron beam within the accelerating waveguide 36 deviates from the central axis of the accelerating waveguide 36 and drive steering coils thereby to reposition the electron beam along the central axis of the waveguide 36. The pickup coils 54 and sensors 56 are inductively and capacitively coupled to the passing electron beam and as mentioned above are positioned at angular positions about the accelerating waveguide 36. The combined inductive and capacitive signals can detect with sufficient accuracy the electron beam position. If the electron beam deviates from the central axis, some of the pickup coils 54 and sensors 56 will see a larger signal, and the rest will have a reduced signal. This signal imbalance is used to create a feedback signal that drives the steering coils. Because both inductive and capacitive coupled sensors are used, the frequency response of the beam steering apparatus 50 can be modified by adjusting either the inductive or capacitive coupling coefficients. This allows the beam steering apparatus 50 to be operated at a frequency range that is not noisy. In order to achieve very good dynamic steering, the pickup coils 54 and sensors 56 are positioned at several positions along the accelerating waveguide 36, and several sets of orthogonal steering coils are used.

In addition to the beam steering apparatus 50, the linac 12 is magnetically shielded by placing a Mumetal® (a commercially available material with very high magnetic permeability) barrier around the electron gun 33 and accelerating waveguide 36 to reduce exposure of the electron beam generated by the linac 12 to magnetic fields as much as possible.

As will be appreciated, changes in the magnetic field present at the linac 12, which effect the electron beam generated therein, can be compensated for dynamically using the beam steering apparatus 50. Furthermore, beam steering does not cause changes in the magnetic field outside the Mumetal® shielding thereby inhibiting the linac 12 from interfering with the MRI apparatus operation.

By fixing the linac 12 and the MRI apparatus 14 to the same gantry 22 so that the MRI apparatus and linac rotate in unison, distortion of the MRI magnetic field is avoided. As will be appreciated, if a magnetically shielded linac that is located in close vicinity to the magnetic field of the MRI apparatus (such that there is magnetic coupling between the linac and MRI apparatus) is rotated independently of the MRI apparatus or vice versa, the movement will affect a change in the magnetic field in the imaging region of the MRI apparatus. This will result in non-homogeneity of the MRI magnetic field, which will result in unacceptable image distortions. By mounting the magnet poles 18 and 20 of the MRI apparatus 14 onto the gantry 22 that is mechanically coupled to the linac 12, the MRI apparatus and linac move together around the subject and so too does the combined MRI magnetic field. Thus, the MRI magnetic field is guaranteed to be constant as a function of gantry angle and image distortion is removed. A counter rotation of the image by means of software permits non-rotated images to be displayed on the screen of the MRI apparatus. The process of shielding the magnetic field at the linac 12 and shimming the MRI magnet may have to be done recursively until settings are found such that the linac 12 is shielded and the magnet has a homogeneous field at its isocenter. However, once this initial setting has been achieved, the need for dynamic compensation with gantry rotation is removed.

Ensuring that the linac 12 and the magnet poles 18 and 20 of the MRI apparatus 14 rotate in unison, avoids the requirement for very complicated dynamic compensation of the MRI magnetic field. Such compensation requires sophisticated modeling of the MRI apparatus and many compensator coils that would have to be dynamically driven by a suitably designed feedback system.

As is known and described previously, the MRI apparatus 14 generates images by reading RF signals that are generated from within the subject being imaged. Transmitted RF pulses tilt the magnetic moments of protons of the tissue to be imaged. The frequency of precession of the protons depends on the magnetic field strength, which are set by gradient magnetic field coils. Phase information is set by applying a second pulse, and then the imaging is accomplished by reading the RF signals from processing protons and reconstructing the image based on the known gradient field. This imaging sequence is done in pulsed operation, with a certain repetition time between imaging sequences.

The linac 12 also functions in a pulsed power mode of operation. The pulses typically have a duration in the range of about 4 μs to 10 μs, with typical repetition frequency of 200 Hz, for a pulse repetition period of 5 ms. The dose rate of the linac 12 is determined by the time-averaged dose rate. The RF pulses from the linac are formed when the high voltage on a bank of capacitors that are coupled by inductors (also referred to as a pulse forming network, or PFN) is discharged through a high voltage switch. The pulse shape depends on the capacitance and inductance of the PFN, and it is normally constructed to have sharp rise and fall times, and a constant voltage in between, in order to behave like a square wave function. These quick voltage increases and decreases are the cause of the high frequency component of RF noise that propagates outside of the linac 12.

The power of the RF pulses transmitted into the patient are significantly higher than the RF noise generated by the linac 12, and so linac pulsing will not affect the transmitted RF pulse. The SAR limit set by the FDA is 0.4 W/kg. Power emitted from the pulsing of the linac is in the mW range. However, the RF signals generated by precessing protons within the subject are very small, and so any noise generated by the linac 12 will significantly interfere with the RF signal read-back process, and likely remove all imaging capability of the MRI apparatus 14.

Figure 5:
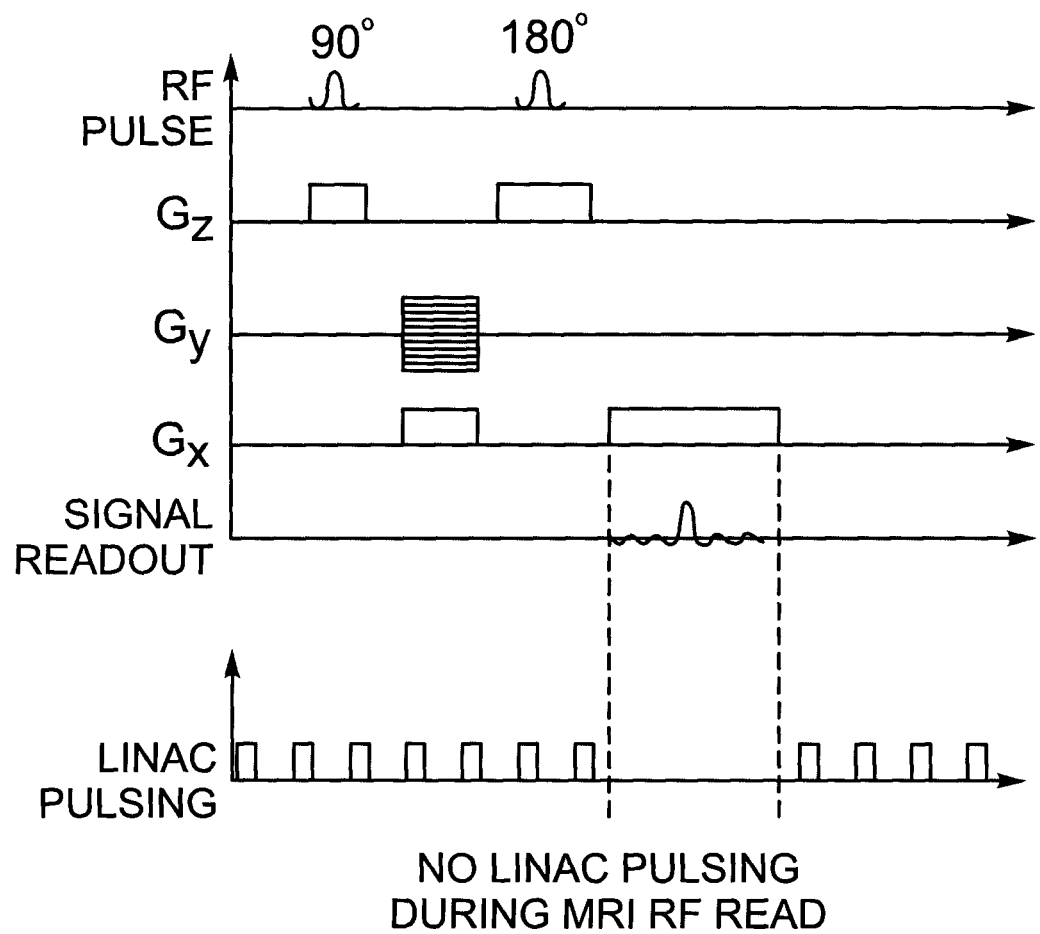
FIG. 5 is a pulse sequence diagram illustrating operation of the integrated linear accelerator and MRI system of FIGS. 1 to 3.

To deal with this problem, timing sequences are used that ensure the linac 12 is not pulsing when the MRI apparatus 14 is reading RF signals back from the patient. FIG. 5 shows exemplary timing sequences. Two approaches are possible. In one approach, the MRI apparatus 14 is altered such that it produces a low voltage signal that indicates when it is about to read RF signals from the patient. This signal is interfaced into the linac 12 and defeats the trigger signals that cause modulator pulses and electron gun pulses. Thus, this creates a quiet RF period where the MRI apparatus 14 can read back RF signals.

Alternatively, in the second approach, entire time periods (on the order of seconds) can be set aside to either MRI imaging or linac pulsing. This approach may be used in systems where the linac interferes with the MRI apparatus when the MRI apparatus is transmitting RF, or if the decay time of RF after a pulse is sufficiently long such that the first approach is not feasible. In this case, the dose rate of the linac 12 and imaging time of the MRI apparatus 14 are reduced, and so a compromise between dose rate and image resolution is needed.

As will be appreciated, preventing linac noise from impeding the MRI apparatus' ability to read RF signals allows imaging and radiotherapy delivery to be performed simultaneously, without interference of the imaging sequence due to the linac.

Figure 6:
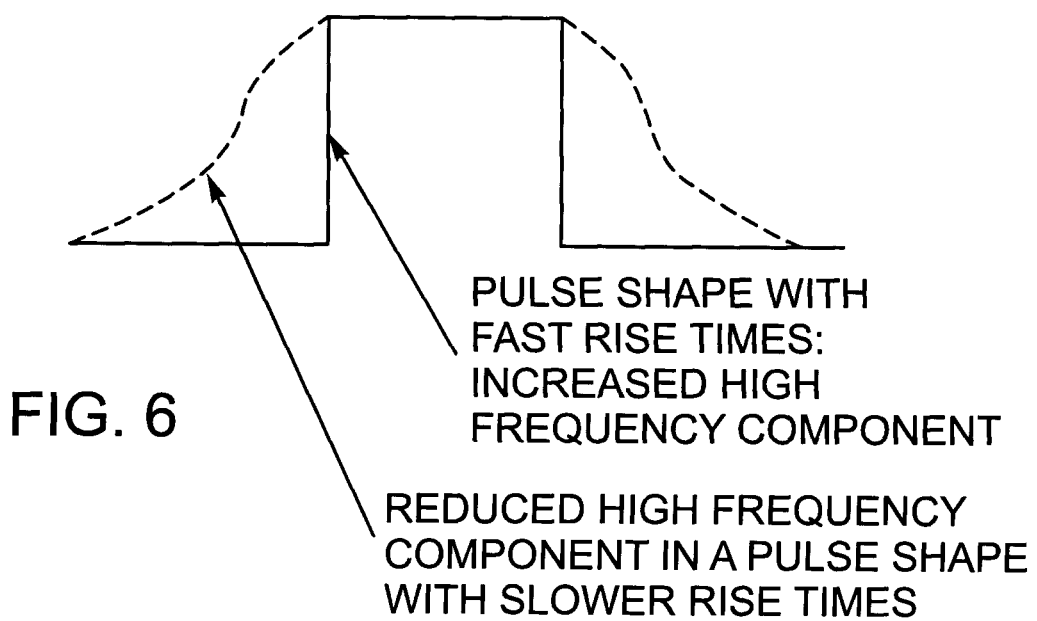
FIG. 6 is a diagram showing the high voltage pulse shapes applied to the linear accelerator.

Reduction in the high frequency component of the RF noise produced by the linac 12 is also performed to reduce interference between the linac and MRI apparatus 14. The high voltage that is applied to the RF generator in the linac is a square wave with high frequency components associated with it. The high frequency components can be removed by appropriate shaping of the high voltage driving pulses. The rise and fall times of the high voltage pulses can be modified by selecting the appropriate capacitance and inductance on the PFN. This is illustrated in FIG. 6. Although a specific driving pulse shape is shown, those of skill in the art will appreciate that a variety of pulse shapes can be constructed. The only limitation on the pulse shape is that a constant voltage region is needed during the time period where the RF generator and electron gun pulse are synchronized such that electrons and RF are introduced into the accelerating waveguide 36 simultaneously. This modification may create a problem with the size of the high voltage pulse since many systems are designed to use the square wave feature of pulsed high voltage to double the nominal voltage of the high voltage generator. As a result a larger high voltage generator may be required.

If desired, in order to reduce RF noise further a Faraday cage can be placed around the entire linac structure to contain noise generated by the linac 12. This includes the pulsed power modulator, transmission and accelerating waveguide and bremsstrahlung heavy metal target. A copper shield can be integrated into the heavy metal target, which may be used in the design of the target in regards to filtration of the x-ray spectrum.

In the above-described example, the MRI apparatus 14 and the linac 12 are mechanically coupled so that magnet poles and the linac rotate in unison. Those of skill in the art will appreciate that other coupling devices that synchronize the magnetic field of the MRI apparatus and the linac to avoid magnetic interference from occurring may be used.

Further, in the above-described embodiment, compensation of residual magnetic fields present at the linac 12 from the magnet of the MRI apparatus 14 is achieved using a dynamic beam steering technique based on feedback from beam position coils. Those of skill in the art will appreciate however that any steering method that uses feedback can be used to position properly the electron beam in the linac.

Also, in the above-described embodiment, the removal of RF interference from the linac 12 in the process of image formation is achieved by imposing certain timing restrictions on the linac pulsing sequence and the MRI apparatus image formation pulse sequence, by modification of the linac high voltage pulse, and by RF shielding. Those of skill in the art will appreciate that other timing sequences may be used to reduce RF interference.

Figure 7:
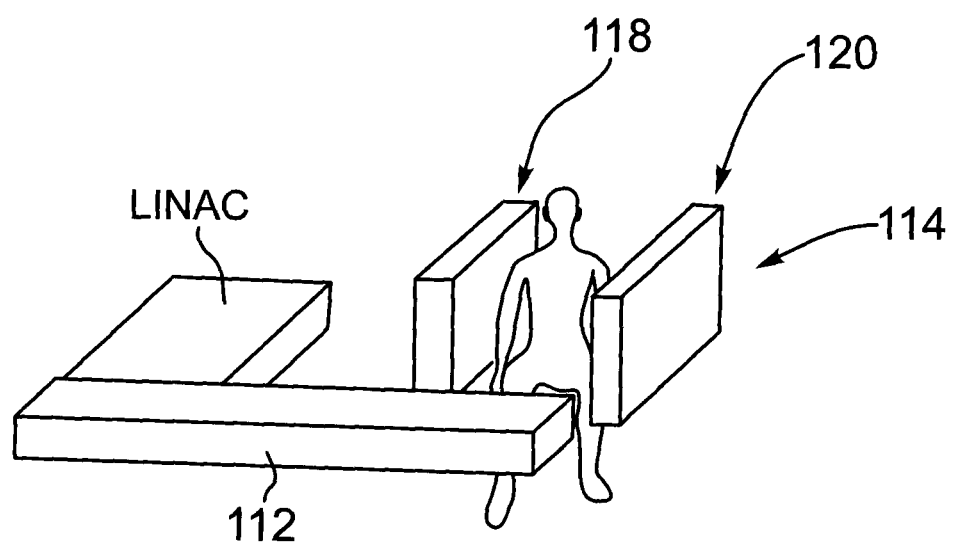
FIG. 7 is an end view of an alternative embodiment of an integrated linear accelerator and MRI system.

Turning now to FIG. 7, another embodiment of an integrated linac and MRI system is shown. In this embodiment, the patient can be treated in a sitting configuration. The linac 112 and MRI apparatus 114 are mechanically coupled so that the electron beam is directed horizontally, and the magnet poles 118 and 120 are mounted vertically such that the magnetic field is horizontal, but perpendicular to the electron beam. These two components are fixed and non-movable. Variable angle electron beam delivery is achieved by rotating the subject that is in a sitting position.

A benefit of this embodiment is the ability to simulate and treat under image guidance, a subject that is unable to lie comfortably in a supine or prone position, for times long enough to allow radiotherapy. This is particularly useful for some lung cancer patients, but would also be useful for other subjects.

Although the MRI apparatus 14 has been described as having a 0.2 T magnetic field strength, those of skill in the art will appreciate that other magnetic field strengths are possible as well as other magnet design types such as a Helmholtz-pair configuration or an open "c" magnet configuration. In these cases, a two-dimensional (2D) imaging device, such as for example a flat panel or other detector array, is placed in-line with the radiation source on the opposite side of the subject to provide megavoltage or core-beam CT images, 2D projection beam verification or 2D-to-3D registration. This configuration has specific application for simulation of radiotherapy treatment and provides megavoltage attenuation data important for treatment planning calculations. In addition, the associated MRI provides simultaneous images that have excellent soft-tissue contrast for target definition. If the radiation source is a diagnostic x-ray tube, CT and MR images can be created simultaneously giving the device broad applications in diagnostic medicine.

In an alternative embodiment, a 2D imaging device suitable for diagnostic nuclear medicine imaging is placed in the opening between the two poles of the magnet to provide SPECT imaging simultaneous to MRI. This configuration utilizes the radiation source that is internal to the subject rather than an external radiation source as described above. As will be appreciated, this arrangement provides additional imaging information useful in diagnostic medicine and treatment planning.

Those of skill in the art will appreciate that since some detector systems can be used for diagnostic CT as well as SPECT, the above described MRI-CT and MRI-SPECT systems can be combined to yield an MRI-CT-SPECT system.

Although the above examples describe the use of a linac, those of skill in the art will appreciate that virtually any radiation source may be used. For example, the radiation source may be another particle accelerator including those that use laser-induced plasmas, that generate electromagnetic radiation (such as photons, x-rays, coherent radiations), electrons, protons, carbon ions, other heavy ions, neutrons or sub-atomic particles such as pi-mesons. Alternatively, the radiation source may be a radioisotope source, a radiation generating device that radiates electromagnetic sound, heat, UV etc. or a source of coherent radiation such as for example a synchrotron.

Although the embodiments have been described herein with reference to the accompanying drawings, it is to be understood that the disclosure is not limited to those precise embodiments, and various other changes and modifications may be affected therein by one skilled in the art without departing from the scope and spirit of the disclosure. All such changes and modifications are intended to be included within the scope of the disclosure as defined by the appended claims.

What is claimed is:
1. A radiation therapy system comprising:
a magnetic resonance imaging (MRI) apparatus;
a radiation source capable of generating a beam of radiation, the radiation source including an accelerating waveguide; and
a coupling to couple the radiation source and the magnetic resonance imaging apparatus such that they rotate in unison about an axis of rotation and the system can be used in a rotation mode, to permit irradiation of a subject from any angle simultaneously with imaging and without reducing magnetic resonance imaging image quality,
wherein the accelerating waveguide is positioned to accelerate particles in a particle beam, such that the particle beam within the accelerating waveguide is perpendicular to the axis of rotation.

2. A radiation therapy system according to claim 1, wherein the entire radiation source is shielded by radio frequency (RF) shielding.

3. A radiation therapy system according to claim 2, wherein the RF shielding comprises a Faraday cage.

4. The radiation therapy system of claim 1 wherein the radiation source is rotatable about a subject without affecting the homogeneity of the MRI apparatus magnetic field.

5. The radiation therapy system of claim 1 wherein the radiation source and MRI apparatus are held stationary, rotation therapy being achieved through rotation of the subject.

6. The radiation therapy system of claim 1, wherein the coupling couples the radiation source and the MRI apparatus so that the radiation source does not affect the magnetic field generated by the MRI apparatus during movement of the radiation source and the MRI apparatus.

7. A radiation therapy system according to claim 1 wherein the coupling mechanically couples a gantry of the radiation source and a gantry of the MRI apparatus.

8. A radiation therapy system according to claim 1 wherein the coupling couples the radiation source and the MRI apparatus to a common gantry.

9. The radiation therapy system of claim 1, further comprising magnetic interference reducing structure to inhibit the MRI apparatus from interfering with the radiation source during operation.

10. A radiation therapy system according to claim 9 wherein said interference reducing structure includes a beam steering apparatus to maintain the position of the particle beam generated by said radiation source.

11. A radiation therapy system according to claim 10 wherein said beam steering apparatus comprises a beam position sensor and steering coil arrangement disposed along an accelerating waveguide of said radiation source.

12. A radiation therapy system according to claim 1, wherein operation of said radiation source and MRI apparatus is timed to inhibit the radiation source and MRI apparatus from interfering with one another during operation.

13. A radiation therapy system according to claim 12 wherein radiation source driving pulses are interrupted during MRI apparatus RF signal reading.

14. A radiation therapy system according to claim 1 further comprising a two-dimensional imaging device.

15. A radiation therapy system according to claim 14 wherein the imaging device captures one of megavoltage axial and computed tomography (CT) images.

16. A radiation therapy system according to claim 15 wherein the megavoltage axial or computed tomography images are captured simultaneously with magnetic resonance (MR) images for beam verification, registration and generation of attenuation data used in treatment planning calculations.

* * * * *